(12) United States Patent
Besselink

(10) Patent No.: US 6,488,710 B2
(45) Date of Patent: Dec. 3, 2002

(54) REINFORCED EXPANDABLE CAGE AND METHOD OF DEPLOYING

(76) Inventor: Petrus Besselink, Gronausetraat 1220, Enschede, 7534 (NL)

( * ) Notice: Subject to any disclaimer, the term of this patent is extended or adjusted under 35 U.S.C. 154(b) by 54 days.

(21) Appl. No.: 09/797,927

(22) Filed: Mar. 2, 2001

(65) Prior Publication Data

US 2001/0032020 A1 Oct. 18, 2001

Related U.S. Application Data

(63) Continuation-in-part of application No. PCT/IB00/00971, filed on Jun. 30, 2000.
(60) Provisional application No. 60/142,252, filed on Jul. 2, 1999.

(51) Int. Cl.[7] .................................................. A61F 2/44
(52) U.S. Cl. ................................ 623/17.15; 623/17.11
(58) Field of Search ........................... 623/17.11, 17.15, 623/17.16, 17.13; 606/61

(56) References Cited

U.S. PATENT DOCUMENTS

| 5,026,373 | A | | 6/1991 | Ray et al. |
| 5,716,416 | A | * | 2/1998 | Lin ............................. 623/17 |
| 5,782,832 | A | | 7/1998 | Larsen et al. |
| 5,919,235 | A | | 7/1999 | Husson et al. |
| 5,976,186 | A | * | 11/1999 | Bao et al. ...................... 623/17 |
| 6,039,761 | A | * | 3/2000 | Li et al. ........................ 623/17 |
| 6,126,689 | A | * | 10/2000 | Brett ........................ 623/17.16 |
| 6,258,094 | B1 | * | 7/2001 | Nicholson et al. ............ 606/84 |

* cited by examiner

Primary Examiner—Nicholas D. Lucchesi
Assistant Examiner—Michael B. Priddy
(74) Attorney, Agent, or Firm—Killworth, Gottman, Hagan & Schaeff, LLP

(57) ABSTRACT

An expandable inter-vertebral prosthesis. The prosthesis takes over the supporting function of the inter-vertebra disc between two adjacent vertebra bodies, and includes one or more cages and a reinforcing element. Upon cage expansion, a hollow central portion of the cage can accommodate the reinforcing element. The reinforcing element, upon expansion, assumes a spiral shape, and substantially fills up the hollow central portion of the cage to provide enhanced load-bearing capability in a substantially longitudinal spinal direction. Hinges in the cage permit expansion and, once the cage has expanded, prevent it from collapsing. Delivery of the cage in an unexpanded condition into an inter-vertebral space is ensured with a restraining tool that engages the hinge members. The cage, reinforcing element and restraining tool are inserted with the aid of a conventional delivery tube.

27 Claims, 8 Drawing Sheets

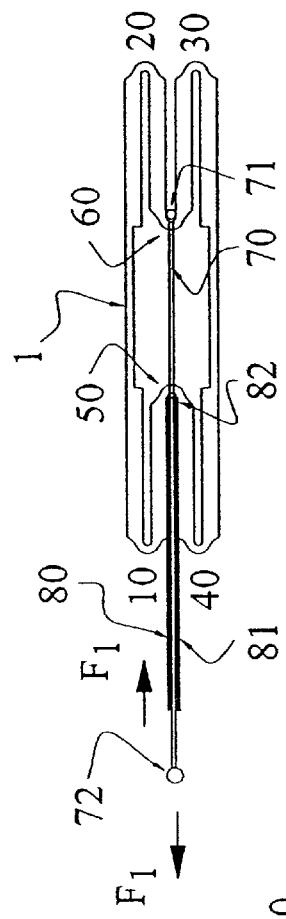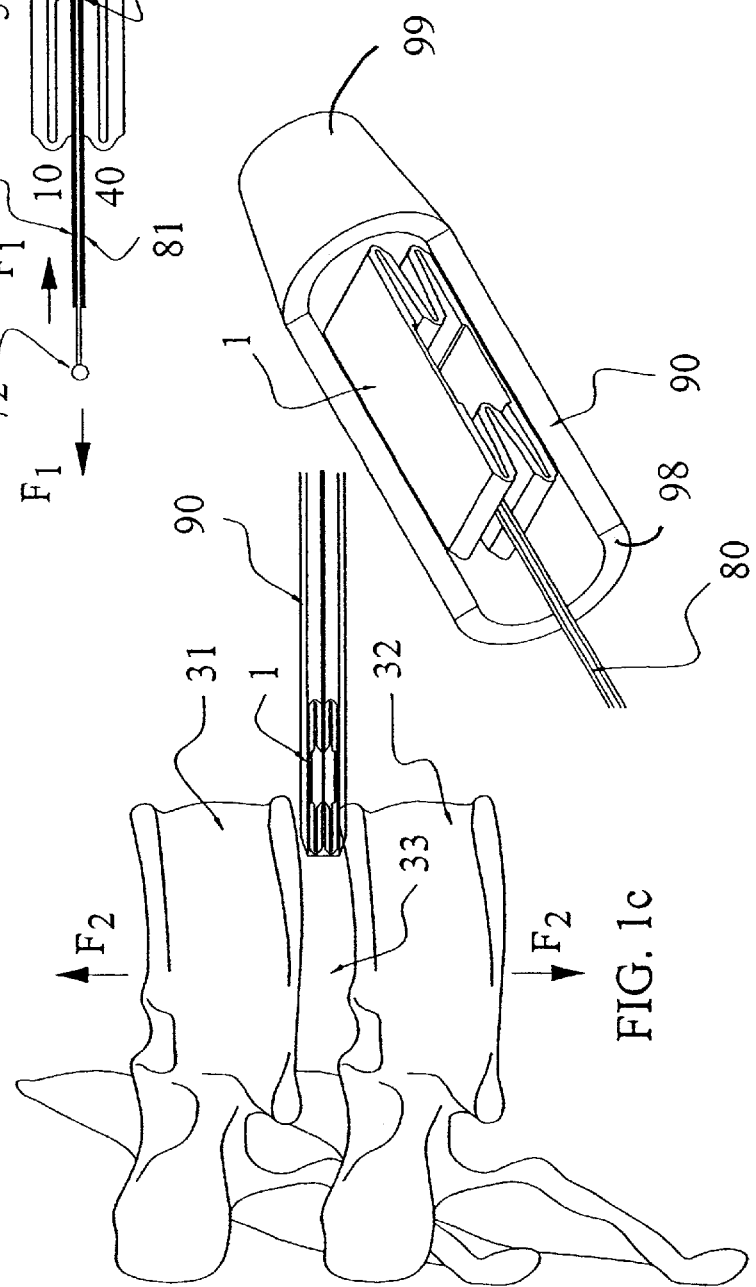

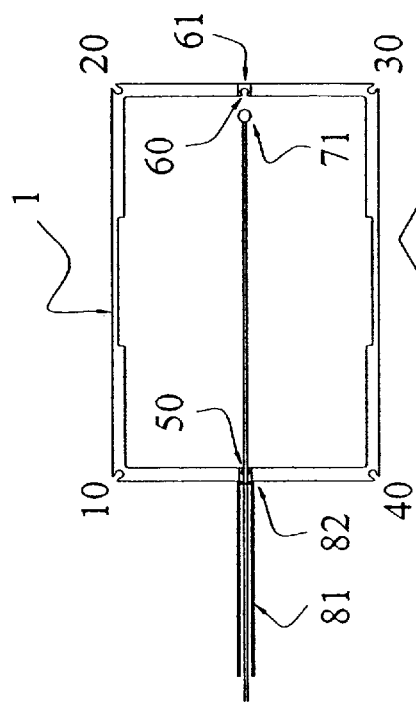
FIG. 2a
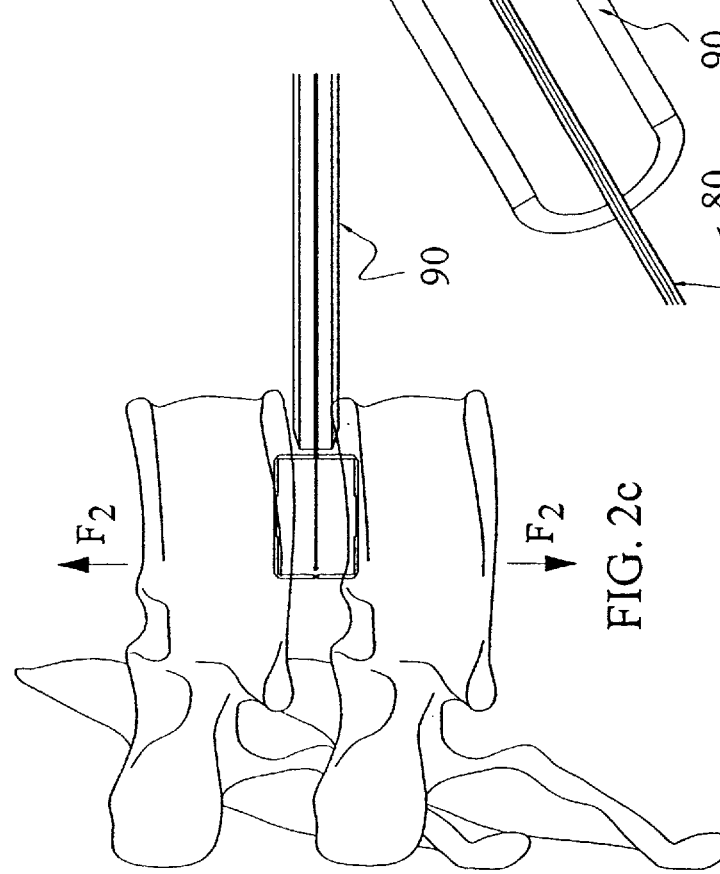
FIG. 2b
FIG. 2c

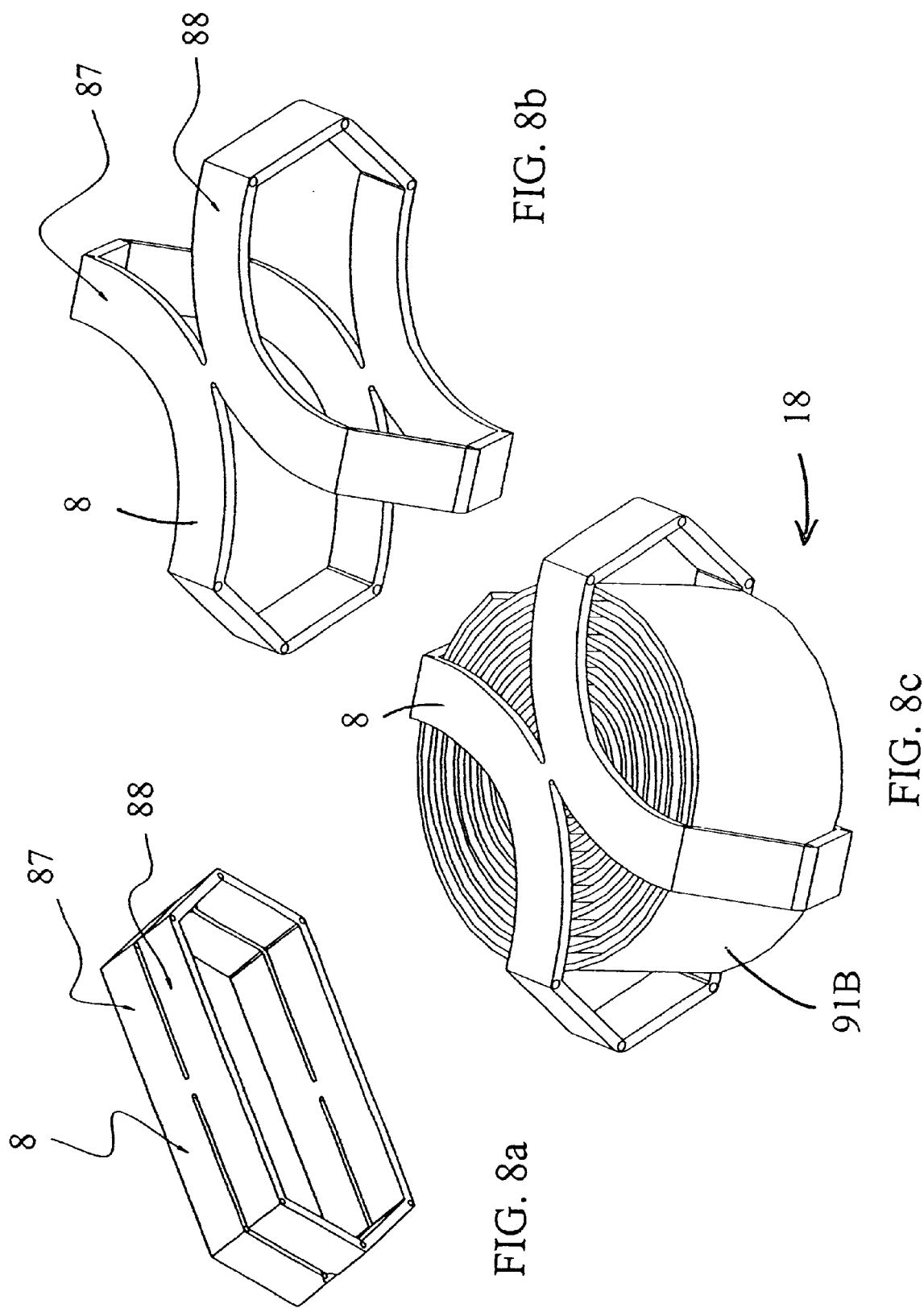

REINFORCED EXPANDABLE CAGE AND METHOD OF DEPLOYING

CROSS REFERENCE TO RELATED APPLICATIONS

This application is a continuation-in-part of PCT/IB00/00971, filed Jun. 30, 2000, which is based on U.S. provisional application Ser. No. 60/142,252, filed Jul. 2, 1999.

BACKGROUND OF THE INVENTION

This application relates to the field of producing an improved spinal prosthesis that is used in surgical procedures, and more particularly to a minimally invasive inter-vertebra expandable cage to replace dysfunctional spinal discs.

Methods to achieve the fusion of two adjacent vertebrabodies are well known in the art. In these procedures, it is necessary to maintain (or regain) the original distance between the vertebra bodies, as otherwise problems, such as nerve damage, may occur. Therefore, it is important to pull or push the vertebra bodies apart during surgery and to place a support that is strong enough to withstand the axial compression forces during normal use. In a human body, these forces can be as high as 1000 N. In conventional spinal fusion procedures, the area of the spine that has to be operated on is approached from the front side, where relatively large incisions have to be made. An example of such a procedure is described in "Subtotal and total vertebral body replacement and interbody fusion with porous Ti—Ni implants", by B. Silberstein in proceedings of SMST-97, Pacific Grove, Calif., USA, on pages 617–621. In this procedure, a rigid porous metal implant is placed between the vertebra bodies, while a tension force is put onto the spine. This method requires a relatively large operation place around the area where the implant must be inserted.

Another method was developed by Krupp Medizintechnik in Essen, Germany, where an expandable ring was made of a nickel—titanium (NiTi) shape memory alloy. This ring was applied in a compressed shape in the inter-vertebra gap and, after insertion, was heated to recover to the programmed height, which resulted in an expansion dimension twice as large as in the compressed state. After placement and expansion, this hollow ring was filled with bone particles and, after several weeks, total fusion was achieved. However, the initial stability of such a ring, in combination with loose bone particles, was very restricted. This necessitated that the patient had to stay relatively immobile for a long time. (See, for example, G. Bensmann et al. in " Üfntersuchungsberichte Krupp Forschungsinstitut", Band 42, 1984, pages 22–38).

SUMMARY OF THE INVENTION

This invention relates to an improved prosthetic device for a minimally invasive permanent spinal fusion that doesn't suffer the limitations of the prior art. In the present context, a spinal fusion procedure is considered "permanent" when the formation of a rigid bone graft between adjacent vertebrae is effected such that it restores spinal functionality to a level approaching that prior to the injury, disorder or disease that necessitated the procedure.

According to an aspect of the present invention, an expandable intervertebral prosthesis for replacement of the nucleus of an intervertebral disc is disclosed. The prosthesis comprises at least one cage made from a relatively thin walled material, and a reinforcing element disposed within a substantially hollow central region of the cage created when the cage is expanded. As used in conjunction with the present disclosure, the term "substantially" refers to an arrangement of elements or features that, while in theory would be expected to exhibit exact correspondence or behavior, may in practice embody something slightly less than exact. The reinforcing element rolls up from an oblong geometry into at least one substantially planar spiral geometry in a force-free state. The reinforcing element occupies the central region of the expanded cage in such a way that stability along a substantially longitudinal axis of the cage is increased, thereby enabling a permanent spinal fusion. In the present context, the longitudinal axis of the cage is substantially aligned with the lengthwise axis of the spine. Accordingly, the vertebrae stack together along the longitudinal, or Z, axis. This axis also defines a longitudinal axis of the intervertebral space.

The reinforcing element may initially have an oblong geometry resembling a strip, which can be of straight or slightly curved cross-section. Upon deployment in the substantially hollow central region of the expanded cage, the oblong shape transforms into a compact body in the shape of a substantially planar spiral. This spiral fills the central region of the cage in such a way that axial stability is increased considerably, while still enabling a permanent spinal fusion. Material choices in both the reinforcing element and the cage may further enhance the utility of the prosthesis. For example, the reinforcing element can be made of any material and form that gives it the capability to be delivered in its initial oblong shape, and then rolled up into its spiral shape in the expanded cage. Examples may include surgical-grade steel, or a shape memory material with superelastic or shape memory behavior. Similarly, the cage can be made of any material and form that give it the capability to be delivered in an collapsed shape and to expand when it is in place. It too can be made from any biocompatible polymer or metal, but preferably of shape memory material with superelastic or shape memory behavior, with their inherently high strain-to-failure ratio. The cage can also be heat-treated to give it the tendency to open up at body temperature by its superelastic properties, and therefore elastic energy will be stored in the cage as long as it is collapsed. In the latter case, the material can be heated above its transformation temperature by means of body heat or any additional heating source. By use of a shape memory cage, the separate restraining tool may not be necessary.

Hinges may be disposed at various locations within the cage to provide preferential bending locations, and thereby facilitate the cage's expansion once it has been deployed in an intervertebral position. These hinges, capable of elastic or plastic deformation, enable both a large expansion ratio and well-defined final cage geometry after expansion. The hinged locations may be formed by any number of conventional methods, including, but not limited to, cutting, grinding, scoring or heat treatment. The hinges may, in the alternate, be conventional pinned hinge members. In addition, the hinges may be configured with mechanical stop or locking features so that once expanded, the cage may settle in to a final expanded state, providing additional longitudinal direction stability and strength. Similarly, one or more apertures may be included in the one or more surfaces of the cage, and may additionally disposed adjacent the hinges. These apertures permit the insertion of an elongate instrument into the unexpanded cage to keep the cage unexpanded until such time as the elongate instrument is released. The elongate instrument comprises an outer tube and a tension wire disposed within the outer tube so that relative movement along the elongate instrument's elongate axis is permitted. To avoid the rapid expansion of the cage, the elongate instrument includes an additional restraining element disposed on the tension wire. This restraining element engages complementary apertures placed within the cage, and keeps the cage in its unexpanded state, even after the cage has left the distal end of the delivery tube. Once the cage is placed in the desired location, the restraining element is gradually released and retracted back into the delivery tube, thus enabling the full expansion of the cage. The unexpanded cage, reinforcing element and elongate instrument can be used with conventional delivery apparatus, such as a delivery tube, to deliver them into the intervertebral space prior to expansion and reinforcement.

One or more of the cages may be combined once they are deployed in the intervertebral space, leading to the formation of an assembled cage. After placement of a first cage, a second cage can be placed in a different position or orientation to construct an assembled cage that provides more support to the vertebrae and gives stability along more directions. Mating surfaces between the first and second cage may include interlocking features, such as grooves, recessions or protrusions to ensure a proper relative placement between the two. The substantially hollow central region within the assembled cage can be defined by the space between the two interconnected cages such that it is bounded by top and bottom walls, and partially bounded by side walls.

According to another aspect of the invention, an expandable intervertebral prosthesis with increased axial stability in a direction substantially parallel with a longitudinal spinal axis is disclosed. The prosthesis includes a first cage in an unexpanded state, a second cage placed inside the first expanded state cage, and a reinforcing element that rolls up from an oblong geometry into at least one substantially planar spiral geometry in a force-free state. The cages are adapted to be placed in an intervertebral position within a spine, and then caused to expand to one or more expanded states. The cages are interconnected such that when both cages are in at least one of their expanded states, they together form an assembled cage, which, in turn defines a substantially hollow central region. The reinforcing element at least partly fills the substantially hollow central region in the assembled cage, thereby forming a reinforced cage.

Optionally, the reinforcing element forms a form-fitted spiral without intervening spaces in the force-free state. In addition, the form-fitted spiral has axial surfaces in substantial contact with corresponding inner surfaces of the cage assembly to enable the cage assembly to take up high axial loads. Moreover, the reinforced cage further comprises sterilizable material with deformation properties corresponding essentially to those of an intervertebral disc to be replaced.

According to another aspect of the invention, an expandable prosthesis for replacement of an intervertebral disc to promote spinal fusion is disclosed. The prosthesis includes at least one cage made from a relatively thin-walled material, and a reinforcing element disposed within a substantially hollow central region defined by at least one the cage. The at least one cage comprises a first, unexpanded state prior to deployment into an intervertebral space, and a second state wherein after deployment in the intervertebral space, the at least one cage is expanded. The reinforcing element comprises a first, oblong state prior to deployment into the substantially hollow central region, and a second state wherein it assumes a substantially planar spiral configuration upon deployment in the substantially hollow central region. The substantially planar spiral configuration at least partly fills the substantially hollow central region in such a way as to improve the stability of the expanded at least one cage in a direction substantially parallel to a longitudinal axis of the intervertebral space.

According to another aspect of the invention, a prosthesis expandable in a plurality of dimensions to promote intervertebral fusion is disclosed. The prosthesis includes a cage and a reinforcing element. The cage further includes a first, unexpanded state prior to deployment into an intervertebral space and a second, expanded state. The second, expanded state itself includes a first expansion in a direction substantially parallel to a longitudinal axis of the intervertebral space thereby defining a substantially hollow central region, and a second expansion in a plane normal to the first expansion such that a space formed by the first and second expansions defines a substantially hollow central region. The reinforcing element includes a first, oblong state prior to deployment into the substantially hollow central region, and a second state wherein the reinforcing element assumes a substantially planar spiral configuration upon deployment in the substantially hollow central region. The substantially planar spiral configuration assumed by the reinforcing element in its second state at least partly fills the substantially hollow central region in such a way as to improve the stability of the expanded cage in a direction substantially parallel to the longitudinal axis of the intervertebral space. Optionally, the cage also includes a plurality of hinges, at least some of which are designed to pivot around an axis substantially parallel to the longitudinal axis of the intervertebral space.

According to yet another embodiment of the invention, a method of using an intervertebral prosthesis is disclosed. The method includes the steps of providing a prosthesis, spreading apart adjacent vertebrae such that an intervertebral space is defined thereby, placing the prosthesis in a delivery tube, inserting the delivery tube into the intervertebral space, controlling the expansion of at least one expandable cage of the prosthesis through limiting the relative movement between the outer tube and tension wire, using the elongate instrument, which is adapted to control the expansion of the at least one expandable cage, to remove the at least one expandable cage from the delivery tube, placing the at least one expandable cage in the intervertebral space, expanding the at least one expandable cage, and inserting a reinforcing element into a substantially hollow central region defined by the expansion of the at least one expandable cage such that the reinforcing element rolls up from an oblong geometry into at least one substantially planar spiral geometry in a force-free state that at least partly fills the substantially hollow central region. The elongate instrument further comprises an outer tube, a tension wire disposed within and relatively movable to the outer tube and a restraining element disposed on the tension wire. The restraining element is further adapted to engage at least a portion of the at least one expandable cage.

It is contemplated that variations in structural features and arrangement of parts may appear to a person skilled in the art without departing from the scope of or sacrificing any of the advantages of the invention. Accordingly, other features and advantages of the invention will be apparent from the following description, the accompanying drawings and appended claims.

BRIEF DESCRIPTION OF THE DRAWINGS

FIG. 1a shows a side view of a collapsed cage and the restraining tool according to an aspect of the present invention;

FIG. 1b shows the collapsed cage and restraining tool of FIG. 1a in a delivery tube;

FIG. 1c shows a side view of two vertebra bodies and a cross section of the assembly of FIG. 1b;

FIG. 2a shows a side view of an aspect of the present invention in an expanded condition with the restraining tool in a released condition;

FIG. 2b shows a perspective view of the expanded cage and released restraining tool of FIG. 2a outside of the delivery tube;

FIG. 2c shows a side view of two unloaded vertebra bodies and a cross section of the assembly of FIG. 2b;

FIG. 7a shows another aspect of the present invention, where a cage is expanded in one dimension, and capable of further expansion in other dimensions;

FIG. 7b shows the cage after expansion in a plane normal to the expanded dimension of FIG. 7a;

FIG. 7c shows the cage of FIG. 7b after its hollow center has been filled with the reinforcing strip to form a reinforced cage;

FIG. 8a shows another aspect of the present invention, where a cage is expanded in one dimension, and capable of further expansion in other dimensions;

FIG. 8b shows the cage after expansion in a plane normal to the expanded dimension of FIG. 8a; and FIG. 8c shows the cage of FIG. 8b after its hollow center has been filled with the reinforcing strip.

DETAILED DESCRIPTION OF THE INVENTION

Figure 3A:
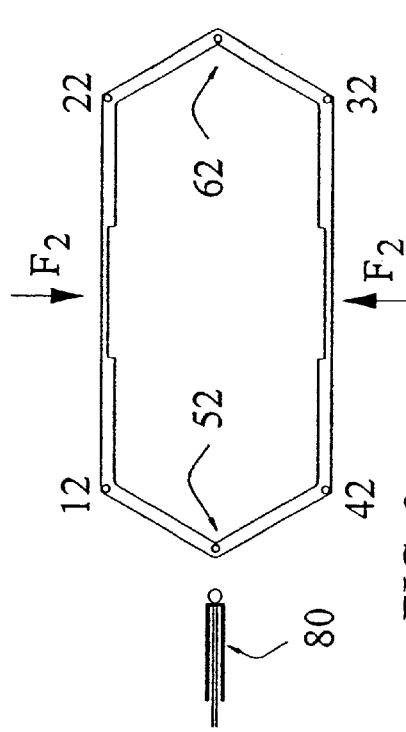
FIG. 3a shows a side view of an expanded cage and a restraining tool in a removed position.

Referring first to FIGS. 1a–1c, a side view of an unexpanded, or collapsed, cage 1 with hinges 10, 20, 30 and 40 at the corners and hinges 50 and 60 in the middle of the left and right planes is shown. While the use of hinges with separate parts is also an option, such as a conventional pinned hinge, this invention preferably includes the use of solid hinges to keep the number of parts as low as possible. Solid hinges can employ preferential bending spots, made by locally cutting, grinding or heat treating the material, and can further be made self-locking after expansion of the cage 1 by means of a mechanical stop in the hinge. An elongate instrument, preferably in the form of a restraining tool 80, contains a tension wire 70 and an outer tube 81. In the preferred embodiment, the distal end 82 of the outer tube 81 acts as a pusher unit, while the tension wire 70 acts as a puller unit. A restraining element 71, preferably in the form of a button or hook, is disposed on a distal end of tension wire 70, and can be engaged to the cage 1 through an aperture 61 near hinge 60. Similarly, a distal end 82 of restraining tool 80 can be pushed against hinge 50. The relative movement between proximal ends 72 of tension wire 70 and outer tube 81 enables the operator to either maintain force F1 to keep hinges 50 and 60 pulled close towards each other, thus bringing and keeping the cage 1 in its unexpanded state, or to release force F1, thus allowing the cage 1 to expand. FIG. 1b shows the unexpanded cage 1 and restraining tool 80 in a delivery tube 90, shown cutaway for clarity. Delivery tube 90 includes a proximal end 98 and distal end 99. The semi-rigid structural nature of delivery tube 90 prevents premature expansion of cage 1. FIG. 1c shows a side view of two vertebra bodies 31 and 32 with the intervertebral disc removed, thus creating a gap 33 to be filled with cage 1, which is inserted into gap 33 through insertion tube 90. Force F2 (shown in FIG. 1c as a tension force) applied to the spine maintains gap 33 during the deployment of cage 1.

Referring now to FIGS. 2a–2c, a side view of cage 1 (now expanded) shows that, upon allowing the relative movement between hinges 50 and 60, made possible through the relative displacement between restraining element 71 on the distal end of tension wire 70 and distal end 82 of outer tube 81. The elastic energy inherent in cage 1 pushes outward, forcing the hinges to return to their released position, coincident with a first expanded state. This in turn permits restraining element 71 to be backed out through aperture 61. The geometry of the restraining element 71 and aperture 61 in hinge 60 is chosen such that restraining element 71 can easily be detached from the hinge 60. For example, the shape change of aperture 61 caused by the elastic deformation of hinge 60 could be such that upon expansion, the aperture 61 assumes a circular or elliptical shape of sufficient cross-sectional area that restraining element 71 is able to pass through aperture 61, thereby becoming automatically released. Similarly, the geometry of the opposing hinge 50 and adjacent aperture 51 (shown in FIG. 3b), has to allow the removal of distal end 71 of the wire, as well as take up the force F1 exerted by outer tube 81. FIG. 2b shows the cage in its first expanded state, along with released restraining tool 80. Outer tube 81 is multifunctional in that it is used as part of restraining tool 80, as well as to push the cage 1 out of delivery tube 90, as shoulders formed on the distal end 82 of outer tube 81 engage the surface of the cage 1 peripherally around aperture 51. FIG. 2c shows a side view of two unloaded vertebra bodies and a cross section of the device of FIG. 2b. The cage 1 has just been pushed out of the delivery tube 90, and the restraining tool 80 has been released. As long as force F1 (shown in FIG. 1a) in the restraining tool 80 is maintained, it is very easy to push the cage out of delivery tube 90, while the friction is negligible, thus allowing precise and simple repositioning of the cage 1.

Figure 3B:
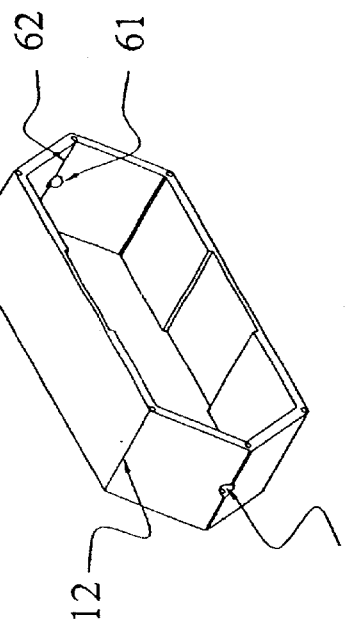
FIG. 3b shows the expanded cage of FIG. 3a with the hinges in locked position after loading.
Figure 3C:
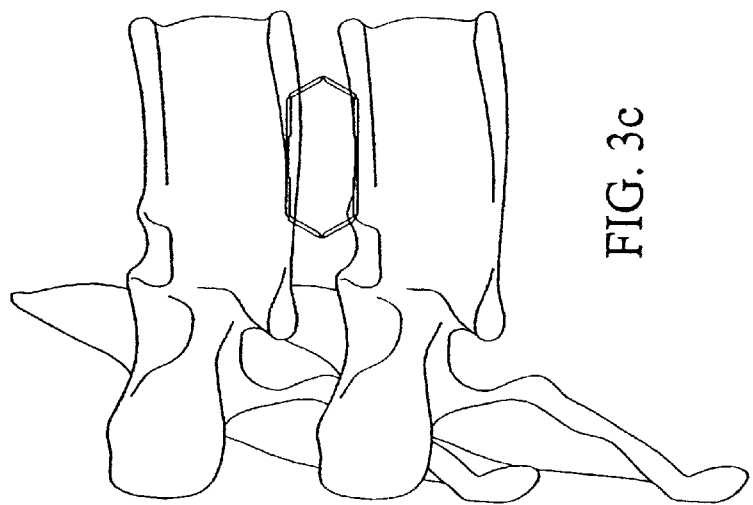
FIG. 3c shows a side view of two loaded vertebra bodies and a cross section of the cage of FIG. 3b.

Referring now to FIGS. 3a–3c, a side view is shown of cage 1, as well as a removed restraining tool 80. By force F2 (shown initially in compression), the cage 1 slightly deforms from the first expanded state of FIGS. 2a–2c until the hinges reach their locked position, thus establishing a second expanded state. For hinges 10, 20, 30 and 40, the respective gaps 12, 22, 32 and 42 close at the outside, while for hinges 50 and 60 the gaps 52 and 62 close at the inside. FIG. 3b shows a perspective view of a loaded expanded cage in its second expanded state with the hinges in locked position.

Apertures 51 and 61 can also be seen. FIG. 3c shows a side view of two loaded vertebrae and a cross section of cage 1. The removal of force F2 at the spine has lead to the loading of the cage 1.

Figure 4A:
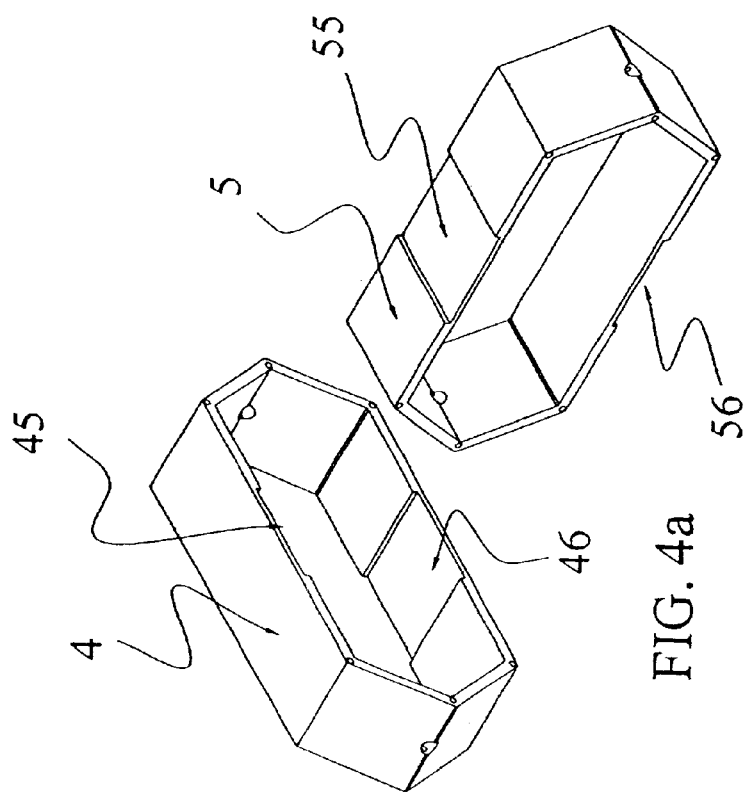
FIG. 4a shows two expanded cages that can be used to build an assembled cage.
Figure 4B:
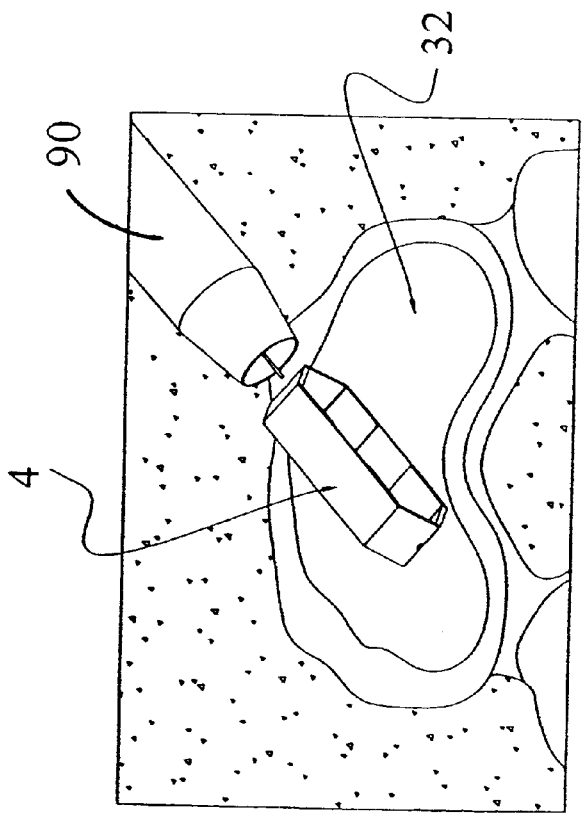
FIG. 4b shows a top view of a vertebra, an expanded cage and a delivery tube just after placement of the cage.
Figure 5A:
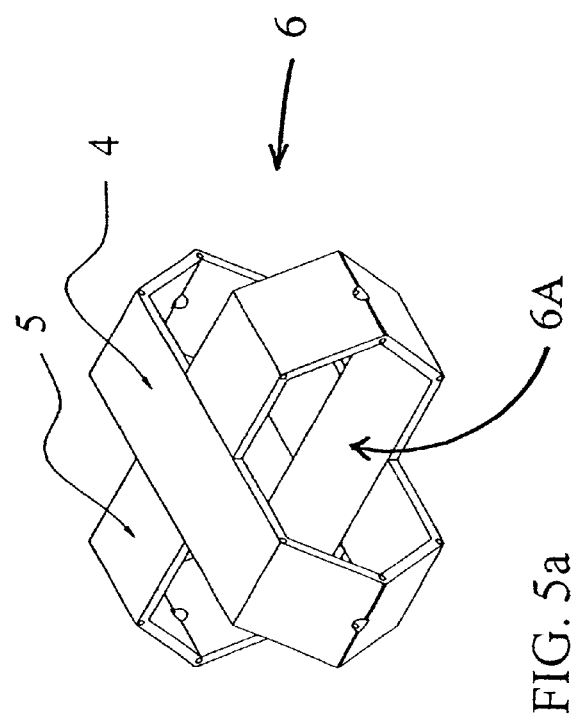
FIG. 5a shows the two expanded cages of FIG. 4a after they have been assembled.
Figure 5B:
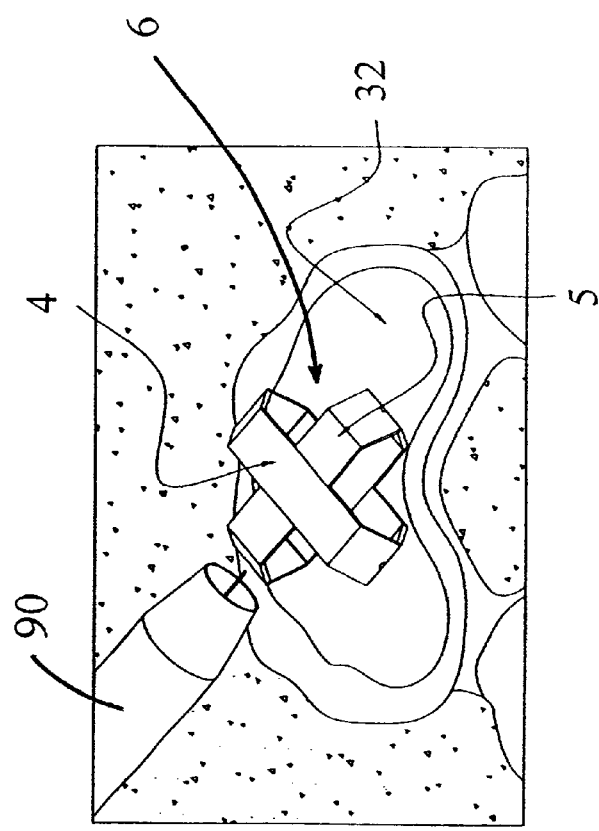
FIG. 5b shows a top view of the vertebra, the assembled cage of FIG. 5a, and the delivery tube just after placement.

FIGS. 4 and 5 show some of the various stages of the deployment and assembly of assembled cage 6, which is made up of two expanded cages 4 and 5. If cage 4 is already in its second expanded state (such that the hinges reach their locked, mechanically stopped positions), cage 5 must first be collapsed and then inserted in a direction perpendicular to the delivery of cage 4. Cage 4 has surfaces 45 and 46 matable with surfaces 55 and 56 of cage 5. The geometry of these surfaces is made so that cages 4 and 5 fit tightly together by the interaction between matable surfaces 45 with 55, and 46 with 56, respectively. FIG. 4b shows a top view of vertebra 32, a first cage 4 and a delivery tube 90 just after placement of the first cage 4. FIG. 5a shows two cages 4 and 5 after they have been expanded to their second expanded state, and put together to form assembled cage 6. A substantially hollow central region 6A is formed within the space defined substantially by the top, bottom and side walls of assembled cage 6. FIG. 5b shows a top view of the vertebra, the assembled cage 6 and the delivery tube 90 just after placement of the second cage 5.

Figure 6B:
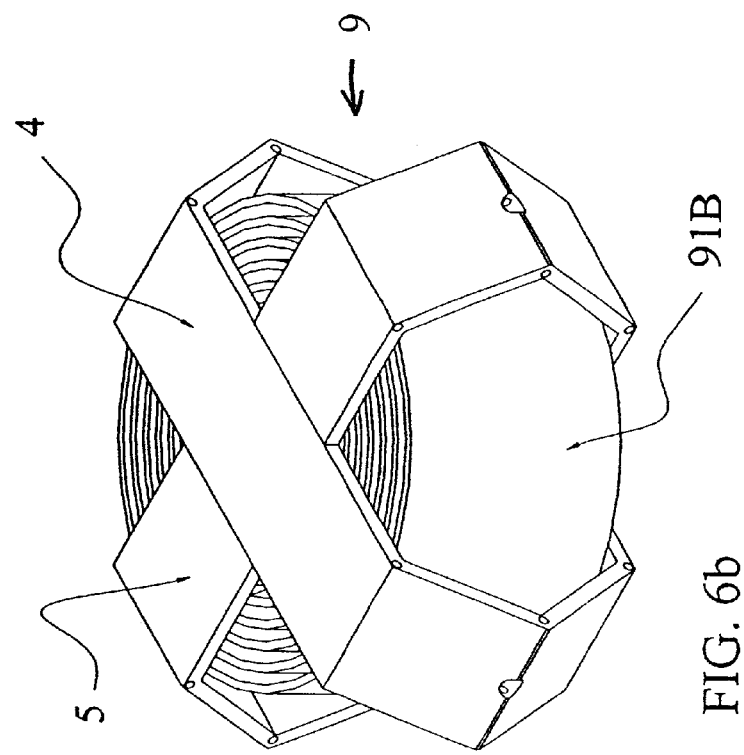
FIG. 6b shows a perspective view of an assembled cage with helical loops of the reinforcing strip disposed within the hollow center.
Figure 6A:
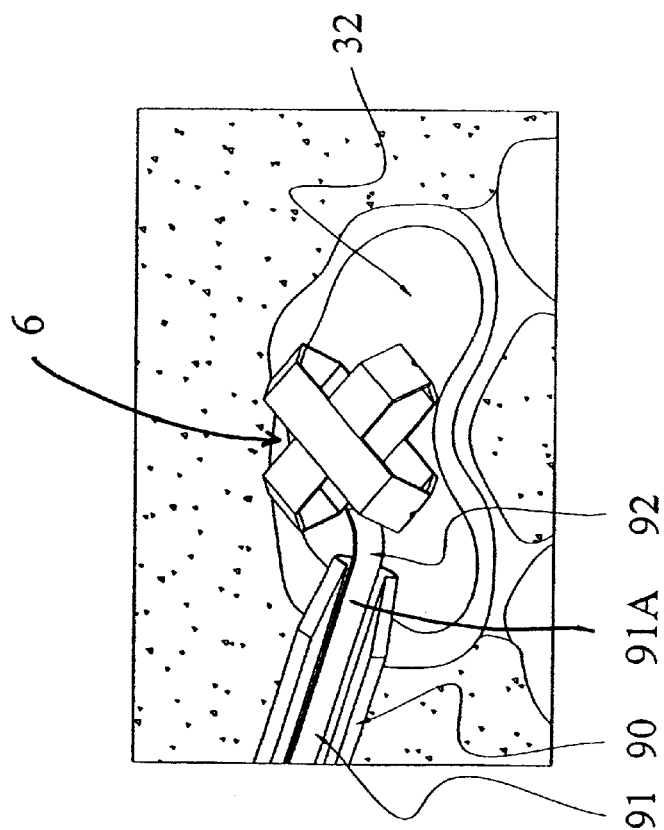
FIG. 6a shows a top view of a vertebra and the insertion from the delivery tube of the reinforcing strip into the hollow center of the assembled cage.

FIGS. 6a and 6b show the introduction of the reinforcing element 91, initially in the form of an oblong strip 91A, into the substantially hollow central region of the assembled cage 6. In the present context, an object is "oblong" when it is in a state where its aspect ratio is such that its extension in one axial dimension is far greater than in another axial dimension. In FIG. 6a, a top view of a vertebra and the insertion from the delivery tube 90 of the reinforcing element 91 into the unloaded assembled cage 6 is shown. The distal end 92 of reinforcing element 91 starts to roll up in the central region 6A of the assembled cage 6. By continuing the insertion, the rest of the reinforcing element 91 can be pushed forward until it is entirely deployed in assembled cage 6. As long as the internal height of the assembled cage 6 is slightly larger than the width of the reinforcing element 91, the reinforcing element 91 can easily be moved around to ensure optimum positioning. After placement of the reinforcing element 91 into central region 6A and removal of force F2 (shown in FIGS. 2c and 3a) from the spine (not shown), the inner surface of assembled cage 6 will rest on the reinforcing element 91, which when fully deployed is of a substantially planar spiral geometry 91B. FIG. 6b shows the combination of assembled cage 6 and the substantially planar spiral geometry 91B of reinforcing element 91 results in a reinforced cage 9. In this stable form, where the inner surface of the assembled cage 6 is pressed against the top and bottom of the substantially planar spiral geometry 91B of reinforcing element 91, even very high axial loads can be applied without plastic deformation of the reinforced cage 9. The reinforcing element 91 can be made of any material and form that will give it the capability to be delivered in an initially oblong shape 91A, and then to roll up into substantially planar spiral geometry 91B upon deployment. Preferably, the reinforcing element 91 can be made of a strip with a curved cross section such that it resembles the well-known measuring tape that easily rolls up in a cylindrical housing. Such a strip, preferably made of a biocompatible material, such as surgical steel or a shape memory material with superelastic or shape memory behavior, can be moved into the assembled cage 6 with a very low insertion force. With a shape memory strip with superelastic behavior, the conversion from the oblong form to the rolled up form will commence as soon as the strip leaves delivery tube 90.

In situations involving a shape memory strip with shape memory behavior, the strip can be heated above its transformation temperature by means of a small heating source in distal end 99 (shown in FIG. 1b) of the delivery tube 90. The shape memory behavior option has the advantage that the friction in delivery tube 90 is lower than with the superelastic behavior option, where the tendency to roll up in the latter is opposed by the inner wall of delivery tube 90 over the entire length of the strip. The heating source can be of any type, comprising radiation, elevated temperature fluid, a Peltier element, or resistive heating.

Figures 7A, 7B, 7C:
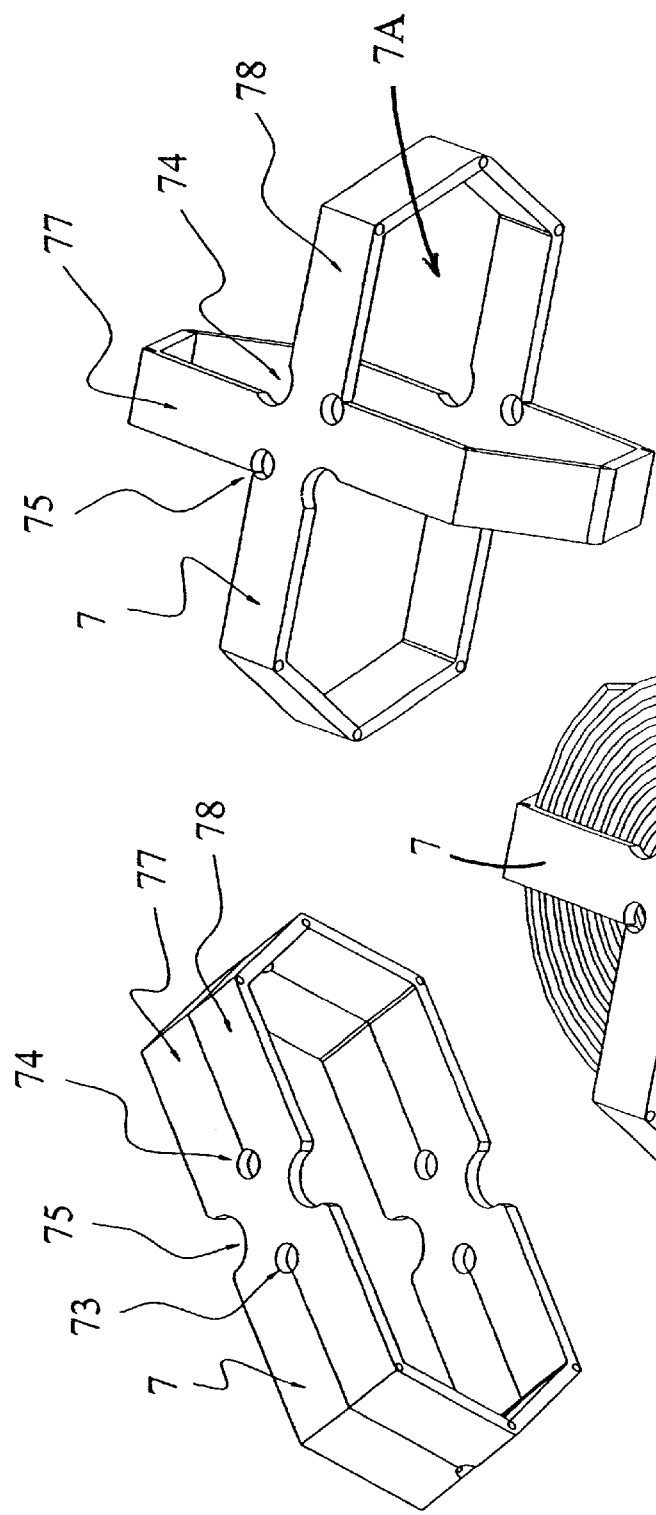

Referring now to FIGS. 7a–7c, FIG. 7a shows a cage 7 expanded in the Z direction, similar to that of previous embodiment expanded cage 1, but with a slightly variant configuration. The top surface of cage 7 has two hinges 73 and 74 that are deformed to a closed position, while hinges 75 and 76 are deformed to an open position. The bottom surface is similar to the top surface, and will therefore not be discussed further. Upon release from the delivery tube 90, the separate arms 77 and 78 of the top surface will move apart to relieve elastic energy. The shape of the hinges 73 to 76 enables a rotation of non-deforming arms 77 and 78. FIG. 7b shows the cage 7 after expansion in the X-Y plane, where the shape of hinges 73 to 76 has changed, and the new geometry of cage 7 gives it more stability against loads along the X and Y directions. FIG. 7c shows the cage 7 after it has been filled with the reinforcing element 91, resulting in reinforce cage 17. Such a single-piece cage has the added benefit of being insertable through a single incision. The hinges 73 and 74 are oriented such that the arms 77 and 78 pivot from them around an axis that is substantially parallel to the longitudinal axis of the intervertebral space.

Referring now to FIGS. 8a–8c, FIG. 8a shows a cage 8 of still another configuration, which, like the previous embodiment of FIGS. 7a–7c, is already expanded into the Z direction. It has additional expansion capability by means of bending in the X-Y plane. Arms 87 and 88 of the top surface are still parallel, but without restraint, they have the tendency to bend in the X-Y plane. The bottom surface of cage 8 is similar to the top surface, and will therefore not be discussed further. In contrary to cage 7 of the previous embodiment, where the hinges absorb the strain due to expansion, arms 87 and 88 of cage 8 deform. FIG. 8b shows the cage 8 after expansion into a fully released state in the X-Y plane. FIG. 8c shows reinforced cage 18, comprising cage 8 and reinforcing element 91 in its substantially planar spiral geometry 91B. It is also possible to make combinations of the aforedescribed embodiments. For example, a cage (not shown), similar to cage 8, can also incorporate hinges such as those employed in cage 7, so that strains due to expansion can be divided between bending members similar to arms 87 and 88 and hinges similar to hinges 74 to 76.

It will be appreciated by those skilled in the art, having regard to this disclosure, that other modifications of this invention beyond these embodiments specifically described here may be made without departing from the spirit of the invention. Accordingly, such modifications are considered within the scope of the invention as limited solely by the appended claims.

What is claimed is:

1. An expandable intervertebral prosthesis for replacement of the nucleus of an intervertebral disc, said prosthesis comprising:

at least one cage made from a relatively thin walled material; and a reinforcing element that rolls up from an oblong geometry into at least one substantially planar spiral geometry in a force-free state that at least partly fills a substantially hollow central region within said at least one cage in such a way that stability along a substantially longitudinal axis of said at least one cage is increased, thereby enabling a permanent spinal fusion.

2. The prosthesis according to claim 1, wherein said at least one cage is configured so that it to can be brought into an intervertebral space in an unexpanded state, and then caused to change shape to at least a final, expanded state.

3. The prosthesis according to claim 2, further comprising at least one aperture disposed within at least one surface of said cage.

4. The prosthesis according to claim 3, further comprising an elongate instrument adapted to facilitate insertion of said at least one cage into said intervertebral space, said elongate instrument comprising:
  an outer tube with a proximal and distal end;
  a tension wire disposed within said outer tube, said tension wire moveable relative to said outer tube; and
  a restraining element disposed on said tension wire, said restraining element adapted to selectively engage said at least one aperture disposed within at least one surface of said cage.

5. The prosthesis according to claim 4, wherein said unexpanded state of said at least one cage is configured so that it can be introduced into said intervertebral space by pushing it through a delivery tube with said elongate instrument.

6. The prosthesis according to claim 5, wherein said restraining element can hold said at least one cage in said unexpanded state at least until said at least one cage is removed from said delivery tube and placed into said intervertebral space.

7. The prosthesis according to claim 6, wherein relative movement between said tension wire and said outer tube permits the release of said at least one cage from said unexpanded state to said expanded state.

8. The prosthesis according to claim 1, wherein said substantially hollow central region is made up of a plurality of cages.

9. The prosthesis according to claim 1, further comprising a plurality of preferential bending spots, said plurality of preferential bending spots configured to act as hinges.

10. The prosthesis according to claim 9, wherein said preferential bending spots are created by either locally cutting, grinding or heat treating the material of said at least one cage, or by the use of an additional hinge pin.

11. The prosthesis according to claim 9, wherein at least some of said preferential bending spots further include an end position to act as a mechanical stop, thereby locking said at least one cage into a stable configuration after expansion.

12. The prosthesis according to claim 1, wherein said at least one cage is expandable in both said longitudinal direction and in a direction perpendicular to said longitudinal direction.

13. The prosthesis according to claim 1, wherein said reinforcing element has the shape of an elongated strip with a flat or slightly curved cross section.

14. The prosthesis according to claim 13, wherein said reinforcing element is selected from a material consisting of a polymer, composite, metal, shape memory material with superelastic behavior, shape memory material with shape memory behavior, and combinations thereof.

15. The prosthesis according to claim 13, wherein said reinforcing element has the tendency to roll up from said oblong geometry to said substantially planar spiral geometry, said tendency caused by elastic energy inherent in said reinforcing element.

16. The prosthesis according to claim 13, wherein said reinforcing element has the tendency to roll up from said oblong geometry to said substantially planar spiral geometry, said tendency caused by a stored shape memory effect that is triggered by a change in temperature that said reinforcing element is exposed to.

17. The prosthesis according to claim 16, wherein said temperature change is caused by resistance heating, radiation, conductive contact with an elevated temperature fluid, a Peltier element, or combinations thereof.

18. The prosthesis according to claim 1, said at least one cage made from a material selected from the group consisting of a polymer, metal, shape memory material with superelastic behavior, shape memory material with shape memory behavior, and combinations thereof.

19. The prosthesis according to claim 1, wherein deformation of said at least one cage or said reinforcing element is selected from the group of deformations consisting of plastic deformation, elastic deformation, superelastic deformation, deformation by shape memory behavior, and combinations thereof.

20. An expandable intervertebral prosthesis with increased axial stability in a direction substantially parallel with a longitudinal spinal axis, said prosthesis comprising:
  a first cage in an unexpanded state, said first cage adapted to be placed in an intervertebral position within a spine, and then caused to expand to an expanded state;
  a second cage placed inside said first cage in said expanded state such that when both said first cage is in said expanded state and said second cage is in an expanded state, they together form an assembled cage, said assembled cage defining a substantially hollow central region; and
  a reinforcing element that rolls up from an oblong geometry into at least one substantially planar spiral geometry in a force-free state to at least partly fill said substantially hollow central region in said assembled cage, thereby forming a reinforced cage.

21. The prosthesis according to claim 20, wherein said reinforcing element forms a form-fitted spiral without intervening spaces in said force-free state.

22. The prosthesis according to claim 20, wherein said spiral has axial surfaces in substantial contact with corresponding inner surfaces of said cage assembly to enable said cage assembly to take up high axial loads.

23. The prosthesis according to claim 20, wherein said reinforced cage further comprises sterilizable material with deformation properties corresponding essentially to those of an intervertebral disc to be replaced.

24. An expandable prosthesis for replacement of an intervertebral disc to promote spinal fusion, said prosthesis comprising:
  at least one cage made from a relatively thin walled material, said at least one cage comprising:
    a first, unexpanded state prior to deployment into an intervertebral space; and
    a second state wherein after deployment in said intervertebral space, said at least one cage is expanded, thereby defining a substantially hollow central region; and
  a reinforcing element disposed within said substantially hollow central region, said reinforcing element comprising:
    a first, oblong state prior to deployment into said substantially hollow central region; and
    a second state wherein said reinforcing element assumes a substantially planar spiral configuration upon deployment in said substantially hollow central region, said substantially planar spiral configuration to at least partly fill said substantially hollow central region in such a way as to improve the stability of said expanded at least one cage in a direction substantially parallel to a longitudinal axis of said intervertebral space.

25. A prosthesis expandable in a plurality of dimensions to promote intervertebral fusion, said prosthesis comprising:
a cage comprising:
  a first, unexpanded state prior to deployment into an intervertebral space; and
  a second, expanded state wherein said second, expanded state comprises at least:
    a first expansion in a direction substantially parallel to a longitudinal axis of said intervertebral space thereby defining a substantially hollow central region; and
    a second expansion in a plane normal to said first expansion such that a space formed by said first and second expansions defines a substantially hollow central region; and
a reinforcing element adapted to be disposed within said substantially hollow central region, said reinforcing element comprising:
  a first, oblong state prior to deployment into said substantially hollow central region; and
  a second state wherein said reinforcing element assumes a substantially planar spiral configuration upon deployment in said substantially hollow central region, said substantially planar spiral configuration to at least partly fill said substantially hollow central region in such a way as to improve the stability of said expanded cage in a direction substantially parallel to a longitudinal axis of said intervertebral space.

26. A prosthesis according to claim 25, further comprising a plurality of hinges, at least some of which are designed to pivot around an axis substantially parallel to a longitudinal axis of said intervertebral space.

27. A method of deploying an intervertebral prosthesis, said method comprising the steps of:
providing a prosthesis, wherein said prosthesis comprises:
  at least one expandable cage that defines a substantially hollow central region upon expansion; and
  a reinforcing element adapted to be disposed within said substantially hollow central region; and
an elongate instrument adapted to control said expansion of said at least one expandable cage, said elongate instrument comprising:
  an outer tube;
  a tension wire disposed within and relatively movable to said outer tube; and
  a restraining element disposed on said tension wire, said restraining element adapted to engage at least a portion of said at least one expandable cage;
spreading apart adjacent vertebrae such that an intervertebral space is defined thereby;
placing said prosthesis in a delivery tube;
inserting said delivery tube into said intervertebral space;
controlling the expansion of said at least one expandable cage through limiting the relative movement between said outer tube and said tension wire;
using said elongate instrument to remove said at least one expandable cage from said delivery tube;
placing said at least one expandable cage in said intervertebral space;
expanding said at least one expandable cage; and
inserting said reinforcing element into said substantially hollow central region such that said reinforcing element rolls up from an oblong geometry into at least one substantially planar spiral geometry in a force-free state that at least partly fills said substantially hollow central region.

* * * * *